US008642259B2

(12) United States Patent
Gratzer et al.

(10) Patent No.: US 8,642,259 B2
(45) Date of Patent: Feb. 4, 2014

(54) METHOD FOR IDENTIFYING SUBSTANCES CAPABLE OF MODULATING THE ACTIVITY OF A TARGET MOLECULE

(75) Inventors: Sabine Gratzer, Grafelfing (DE); Meltsje De Hoop, Hofheim (DE); Bernhard Mai, Eichenau (DE)

(73) Assignee: Sanofi-Aventis Deutschland GmbH, Frankfurt (DE)

(*) Notice: Subject to any disclaimer, the term of this patent is extended or adjusted under 35 U.S.C. 154(b) by 468 days.

(21) Appl. No.: 10/625,085

(22) Filed: Jul. 23, 2003

(65) Prior Publication Data
US 2004/0092474 A1  May 13, 2004

Related U.S. Application Data

(60) Provisional application No. 60/430,258, filed on Dec. 2, 2002.

(30) Foreign Application Priority Data

Jul. 23, 2002  (DE) .................................. 102 33 516

(51) Int. Cl.
*C12Q 1/68* (2006.01)
*C12Q 1/02* (2006.01)
*C12N 1/00* (2006.01)

(52) U.S. Cl.
USPC ............ 435/6.1; 435/6.13; 435/6.18; 435/29; 435/254.1; 435/254.11; 435/254.21; 435/255.1; 435/255.2

(58) Field of Classification Search
None
See application file for complete search history.

(56) References Cited

U.S. PATENT DOCUMENTS

| | | | |
|---|---|---|---|
| 5,691,188 A | 11/1997 | Pausch et al. | |
| 5,728,534 A | 3/1998 | Mendelsohn et al. | |
| 5,885,769 A | 3/1999 | Kumar | |
| 6,063,578 A * | 5/2000 | Barbosa et al. | 435/6 |
| 6,602,699 B2 | 8/2003 | Kozian et al. | |
| 2005/0118690 A1* | 6/2005 | Roberts et al. | 435/135 |

FOREIGN PATENT DOCUMENTS

| | | |
|---|---|---|
| EP | 0708 922 B1 | 3/1999 |
| EP | 0974649 A1 | 1/2000 |
| WO | WO 95/21925 | 8/1995 |
| WO | WO 99/14344 | 3/1999 |
| WO | WO 00/12704 | 3/2000 |

OTHER PUBLICATIONS

Crossin et al, Glucocorticoid receptor pathways are involved in the inhibition of astrocyte proliferation, PNAS 15: 2687-2692, 1997.*
Keating et al, Transcriptional downregulation of ATM by EGF is defective in ataxia-telangiectasia cells expressing mutant protein, Oncogene 20: 4281-4290, 2001.*
Yang et al. Improved Fluorescence and Dual Color Detection with Enhanced Blue and Green Variants of the Green Fluorescent Protein. J. Biol. Chem. 273(14): 8212-8216, 1998.*
Tanaka et al. Digitonin enhances the antitumor effect of cisplatin during isolated lung perfusion. Ann Thorac Surg. Oct. 2001;72(4):1173-8.*
Spain et al., "Truncated Forms of a Novel Yeast Protein Suppress the Lethality of a G Protein α Subunit Deficiency by Interacting with the β Subunit" 270(43) The Journal of Biological Chemistry 25435-25444 (1995).*
Leplatois et al. "Neurotensin induces mating in *Saccharomyces cerevisiae* cells that express human neurotensin receptor type 1 in place of the endogenous pheromone receptor" 268 European Journal of Biochemistry 4860-4867 (2001).*
Zhang et al. "Suppresson of a dominant G protein β-subunit mutation in yeast by a Gα protein expression" 9(4) Molecular Microbiology 813-821 (1993).*
A.J. Brown et al., Functional coupling of mammalian receptors to the yeast mating pathway using novel yeast/mammalian G protein alpha-subunit chimeras, Yeast, vol. 16, 2000, pp. 11-22.
B.R. Conklin et al., Substitution of three amino acids switches receptor specificity of Gqalpha to that Gialpha, Nature, vol. 363, 1993, pp. 274-276.
D. Mumberg et al., Yeast vectors for the controlled expression of heterologous proteins in different genetic backgrounds, Gene, vol. 156, 1995, pp. 119-122.
E.M. Kajkowski et al., Investigation of Growth Hormone Releasing Hormone Receptor Structure an Activity of Using Yeast Expression Technologies, J. of Receptor & Signal Transduction Research, vol. 17, 1997, pp. 293-303.
L.A. Price et al., Functional Coupling of a Mammalian Somatostatin Receptor to the Yeast Pheromone Response Pathway, Molecular and Cellular Biology, vol. 15, No. 11, Nov. 1995, pp. 6188-6195.
L.A. Price et al., Pharmacological Characterization of the Rat A2a Adenosine Receptor Functionally Coupled to the Yeast Pheromone Response Pathway, Molecular Pharmacology, vol. 50, 1996, pp. 829-837.
M. Cismowski et al., Genetic screens in yeast to identify mammalian nonreceptor modulators of G-protein signaling, Nature Biotechnology, vol. 17, Sep. 1999, pp. 878-883.
M.H. Pausch, G-protein-coupled receptors in *Saccharomyces cerevisiae*: high-throughput screening assays for drug discovery, Trends in Biotechnology, vol. 15, No. 12, Dec. 1997, pp. 487-494.
N. Ancellin et al., Differential Pharmacological Properties and Signal Transduction of the Sphingosine 1-Phosphate Receptors EDG-1, EDG-3 and EDG-5, Journ. of Biological Chemistry, vol. 274, No. 27, Jul. 2, 1999, pp. 18997-19002.
R.M. Campbell et al., Selective A1-Adenosine Receptor Antagonists Identified Using Yeast *Saccharomyces cerevisiae* Functional Assays, Bioorganic & Medicinal Chemistry Letters vol. 9, 1999, pp. 2413-2418.
R.M. Fredrickson, Budding actors in mammalian G-protein signaling, Nature Biotechnology, vol. 17, Sep. 1999, pp. 852-853.
NM 000623.
NM 000738.
NM 000740.
NM 001050.
NM 001400.
NM 004230.
International Search Report WO2004/019036 dated Mar. 4, 2004.

* cited by examiner

*Primary Examiner* — Hennifer Dunston
*Assistant Examiner* — Nancy J Leith
(74) *Attorney, Agent, or Firm* — Michael G. Biro, Esq.; Lathrop & Gage LLP

(57) ABSTRACT

The present invention relates to methods for identifying substances capable of influencing the activity of a target molecule affecting cellular proliferation.

12 Claims, 15 Drawing Sheets

METHOD FOR IDENTIFYING SUBSTANCES CAPABLE OF MODULATING THE ACTIVITY OF A TARGET MOLECULE

This application claims benefit to under 35 U.S.C. §119 of U.S. Provisional Application No. 60/430,258, filed on Dec. 2, 2002, and German Patent Application 10233516.8-41, filed Jul. 23, 2002, wherein said application are hereby incorporated by reference.

The present invention relates to a cellular method for identifying substances capable of influencing the activity of a target molecule.

The development of novel pharmaceuticals which act on cellular target molecules conventionally uses biochemical or cellular functional assays which enable a multiplicity of putative active substances to be studied for whether they have an effect on the target molecule to be studied.

Cellular assays conventionally function on the basis of growth-based test systems in which the activity of the target molecule to be studied has an effect on cell propagation. In addition, test systems are known in which the activity of the target molecule is detectable and quantifiable on the basis of the activity or expression of "reporter gene products". Although both types of assays allow novel active substances which modulate the activity of the target molecule to be identified even in high throughput screening (HTS), the disadvantage of these known test systems is their usually relatively low signal-to-background ratio so that their specificity is very low, in particular when used in the HTS format.

In view of the disadvantages of the prior art mentioned it is the object of the invention to provide a test system which allows highly efficient screening in HTS format.

According to the invention, this object is achieved by a cellular method for identifying substances capable of influencing the activity of a target molecule, with the cells to be analyzed carrying at least one reporter gene and the activity of that target molecule having an effect on cell propagation, which comprises the steps:
  a. contacting at least one cell with the substance to be tested,
  b. detecting cell propagation,
  c. detecting the activity of the reporter gene product.

The detection of cell propagation and that of the reporter gene activity need not necessarily be in the above order.

The reporter gene may be integrated into the genome of the cell or be stably or transiently transfected into said cell. The term reporter gene product comprises both the mRNA and the protein. Suitable reporter genes and products thereof are sufficiently well known to the competent skilled worker, and particularly suitable here are enzymes such as β-galactosidase, β-glucuronidase, luciferase, alkaline phosphatase, acidic phosphatase or fluorescent proteins such as GFP, BFP, aequorin, and the like. Suitable promoters for the reporter genes depend on type and target of the specific test system and on the cell type used. The reporter genes are preferably under the control of promoters which are regulated via the signal transduction pathway to which the target molecule couples directly or indirectly. Preference is given to reporter genes whose products are enzymes whose activity is detectable on the basis of converting an externally added substrate.

The target molecules within the scope of the invention may have a direct or indirect effect on the propagation of the cell used. In this connection, it is possible for the target molecule to exert influence on propagation of the cell used for the method (and thus, in the active state, to directly activate or inhibit said cell). The target molecule may be, for example, constitutively active and be inhibited by the substance to be tested or may be present in an inactive state and be activated by the substance to be tested. According to a preferred embodiment, however, the target molecule exerts influence on the propagation of the cell to be used in the method in the active state only by interposition of a molecule which directly influences said propagation (e.g. FUS1-HIS3 in yeast cells, see below). In principle, all types of extracellular, membrane-bound or intracellular biological molecules are suitable as target molecules, particular preference being given to human biomolecules, in particular proteins or nucleic acids, among these in particular members of signal transduction cascades of cell division, in particular GPCRs, protein kinases, protein phosphatases, etc.

The influence of the substance to be analyzed on the target molecule may promote or inhibit the activity of the latter, for example by interaction with the target molecule itself or by influencing molecules which themselves have an effect on the activity or expression of the target molecule.

Cell propagation and reporter gene product activity may be detected purely qualitatively or else quantitatively, and various types of detection are commonly known to the competent skilled worker (for example measuring cell density directly or indirectly by determining the turbidity of liquid cultures in the case of cells in suspension, calorimetric or luminometric determinations of reporter gene product activity, etc.).

According to a preferred embodiment, the activity of the target molecule has an effect on the activity, preferably the expression, of the reporter gene product. Said target molecule may act on the activity or expression of the reporter gene product directly (the target molecule itself influences the activity/expression of the reporter gene product) or indirectly (the target molecule influences reporter gene activity or expression via a cellular metabolic or signal cascade activated by said target molecule).

The target molecule is preferably a heterologous molecule (i.e. a molecule not naturally present or expressed in the cells used for the method of the invention) particularly preferably an oligonucleotide, polynucleotide, nucleic acid, polypeptide, protein or protein fragment. The heterologous target molecule may be integrated into the genome of the cell or be stably or transiently transfected into said cell; expression of the target molecule may be constitutive or inducible.

According to a preferred embodiment, the heterologous target molecule acts on propagation of the cell used for the method by interaction with a chimeric molecule. Particular preference is given here to a method in which the heterologous target molecule is a human molecule which is stably integrated into the genome of a nonhuman cell, in particular a yeast cell, and which influences cell propagation via a chimeric molecule which is capable of interacting with the heterologous molecule and integrating into the signal transduction cascades or metabolic cascades intrinsic to the yeast cell. Particular preference is given here to the chimeric molecule being a recombinant protein, polypeptide or protein fragment whose amino acid sequence has human and yeast portions. Particularly suitable within the scope of the invention is the combination of a human GPCR as heterologous target molecule with a chimeric G protein subunit ("transplant", see below), it being in principle possible for any of the subunits to be present in chimeric form.

When using a reporter gene product whose activity is determined on the basis of converting a substrate, it is expedient to add the substrate with a delay after addition of the substance to be analyzed. Preferably the time interval between the addition of the substance to be analyzed and that of the substrate is at least the time for the cell used for the method to complete one cell cycle, with particular preference being given to an interval of from 2 to 24 completed cell cycles. When using yeast cells, the time interval is preferably approx. 4 to 48, preferably 20 to 30, and in particular 24, hours.

The activity of the reporter gene is preferably detected by disrupting the cell, particularly preferably by adding a substance which permeabilizes or destroys the cell wall (expediently a detergent or a combination of two or more detergents; particularly suitable here are digitonin, Triton X-100, Nonidet P-40, Tween 20, CHAPS or SDS). Particular preference is given to digitonin in the concentration range from 10 to 600, preferably 20 to 400, and particularly preferably from 40 to 60, pg/ml and/or to Triton X-100 in the concentration range from 0.005 to 0.4, preferably 0.01 to 0.2, % by volume, in each case based on the final concentration. The detergents are added to the reaction mixture preferably in buffer solutions, particularly suitable buffer conditions being sufficiently well known to the competent skilled worker (physiological buffers, neutral pH, isotonic salt concentration, etc.).

A very wide variety of cell types may be used for the method of the invention: thus, in principle, both prokaryotic and eukaryotic, plant or animal cells are suitable. However, preference is given to eukaryotic cells, particularly preferably mammalian cells or yeast cells, in particular *S. cerevisiae* strains.

According to another preferred embodiment of the invention, various cells are used and simultaneously screened in a single approach or process run, said cells differing from one another by at least the type of target molecule ("multiplex method").

According to a particularly preferred embodiment, the invention relates to a widely usable method for identifying substances which act as ligands for cloned G protein-coupled receptors. The method of the invention so sensitive and robust that it is possible to assay a plurality of GPCRs at the same time in a high throughput assay in multiplex format.

The invention is further illustrated below on the basis of exemplary embodiments and figures.

EXAMPLES

Example 1

Screening for Substances Acting on the Activity of G Protein-Coupled Receptors

One of the most important classes of target molecules for the pharmaceutical industry is G protein-coupled receptors. In the past, numerous representatives of this protein family have gradually been cloned and pharmacologically characterized. Since the whole human genome has now been sequenced, a large number of GPCRs have been identified recently at the sequence level. A major objective of the pharmaceutical industry is now to identify ligands for these receptors by screening comprehensive libraries of substances. Unfortunately, with the currently methods and techniques, a substantial obstacle to finding substances is the time and cost demands that the screening of said libraries with regard to such numerous target molecules entails. EP 0 708 922 B1 discusses the possibility of screening a plurality of GPCRs simultaneously in cell culture. The mammalian cells described there, which overexpress GPCRs, respond with increased growth when contacted with a substance activating the receptor. Since the cells which do not express receptors activated by said substance continue to grow nevertheless, albeit more slowly, the sensitivity of the test system is not very high. Moreover, the method is time-consuming, since the incubation times are very long, and expensive, since it is a mammalian cell system.

One possibility of screening GPCR inexpensively is the use of a test system based on yeast. Since time is also an extremely important factor in pharmaceutical research, it was the objective of the present invention to devise a yeast system which makes it possible to screen numerous GPCRs simultaneously. In order to permit use in high throughput screening, the method should be very easy to manage and have a very large measurement window.

G protein-coupled receptors (GPCRs) play an important part in a multiplicity of physiological processes. They are one of the most important protein families known yet and it is assumed that about 1 000 genes code for this receptor class in the human genome. GPCRs have a characteristic structure: they are integral membrane proteins which wind in the form of α-helices seven times through the phospholipid bilayer of the cell membrane, arranging themselves in a circular pattern. It is estimated that approximately 50% of the pharmaceuticals currently available through prescription bind to GPCRs. This underlines the importance of this receptor class for the pharmaceutical industry. Owing to the size and importance of said protein family and in view of the fact that chemical binding partners are still unknown for many GPCRs (orphan GPCRs), it can assumed that this receptor class will be one of the most important reservoirs for suitable target proteins in the search for novel medicinal substances in the future.

All G protein-coupled receptors act according to a common basic principle: binding of an extracellular ligand leads to confirmational change in the receptor protein so that the latter can contact a guanine nucleotide-binding protein (G protein). The G proteins which are located on the cytoplasmic side of the plasma membrane mediate the extracellular signal to the cell interior. Depending on the specificity of the receptor, they can trigger various signal transduction pathways, all of which lead to the formation of second messengers such as, for example, cAMP, cGMP, $Ca^{2+}$ or others, which trigger reactions in the cell via activation or deactivation of intracellular proteins. The heterotrimeric G proteins comprise three subunits, α, β and γ. In the G protein heterotrimer GDP is bound to the Gα subunit. Interaction with a ligand-activated receptor results in GDP being replaced by GTP. The confirmational changes resulting therefrom lead to the G protein heterotrimer dissociating into an α subunit and a βγ complex. Both the activated a subunit and the βγ complex can influence intracellular effector proteins. The a subunits can be divided into four different classes: Gαs, Gαi, Gαq and Gα12.

GPCRs are classified according to the G protein involved in the signal transduction, i.e. GPCRs of the Gs family mediate adenylate cyclase stimulation via activation of Gαs and thus increase the intracellular cAMP concentration. GPCRs of the Gi family mediate adenylate cyclase inhibition via activation of Gαi, thus decreasing the concentration of intracellular cAMPs. GPCRs of the Gq family mediate stimulation of various PLCβ isoforms via activation of Gαq and lead to hydrolysis of membrane-bound phosphatidylinositol 4,5-bisphosphate to give diacylglycerol and inositol trisphosphate ($IP_3$). $IP_3$ releases $Ca^{2+}$ from intracellular stores. Gα12 interacts with rho-specific guanine-nucleotide exchange factors.

The signal is maintained until the Gα subunit which has a GTPase activity hydrolyzes the bound GTP. Members of the family of RGS (regulator of G protein signaling) proteins control the duration of the signal by acting as activators on the GTPase activity of the Gα subunit. This G protein-controlled signal transduction system seems to be common to all eukaryotic systems.

A very well characterized example of such a signal system is the "pheromone response pathway" of baker's yeast, *Saccharomyces cerevisiae*. Yeast cells having the MATa mating type express a receptor encoded by the STE2 gene. This receptor is activated by binding of α factor, a peptide pheromone which is released by yeast cells of the other mating type (MATα). The heterotrimeric G protein of yeast is composed of the products of the genes GPA1 (Gα), STE4 (Gβ) and STE18 (Gγ). The Gβγ complex is released after activation of the Ste2p receptor and transfers the signal to a mitogen-activated protein kinase cascade. This leads to activation of the cyclin-dependent kinase inhibitor Far1p, resulting in cell cycle arrest and transcription induction of a number of genes involved in the mating process (e.g. FUS1). This pathway is desensitized by Sst2p, a member of the RGS family. Yeast cells of the other mating type (MATα) express a different receptor (Ste3p) and therefore respond to the other pheromone (a-factor) released by MATa cells. Apart from this, the signal apparatus used by the two mating types is identical.

It has been demonstrated several times that mammalian GPCRs can be coupled to the G protein signal system of yeast. Some receptors, including rat somatostatin 2 receptor (Price et al., Mol Cell Biol 15, 6188-6195 (1995)) and rat adenosin $A_2a$ receptor (Price et al., Molecular Pharmacology 50, 829-837 (1996)) can interact directly with the yeast Gα protein Gpa1p, whereas other receptors, including growth hormone releasing-hormone receptor (GHRHR) (Kajkowski et al., J Recept Signal Transduct Res 17, 293-303 (1997)) are incompatible with Gpa1p. In order to enable these receptors to couple nevertheless, the yeast Gα subunit can be deleted, and the heterologous receptor is instead expressed together with the full-length mammalian Gα subunit. As an alternative to this, hybrid Gα subunits have been used in which the C-terminal domain (approximately one third of the peptide sequence) of Gpa1p has been replaced by the corresponding region of the mammalian Gα subunit; see WO 95/21925 for both approaches. Hybrids or other modified or heterologous Gα subunits need to fulfil a few criteria in order to be able to couple to the yeast signal transduction system. The most important one is for said subunits to be capable, on the one hand, of binding efficiently to yeast Gβγ, in order to be able to thus prevent a signal in the absence of an activated GPCR, and, on the other hand, of binding effectively to the receptor activated by an agonist, in order to then be able to transduce the signal. Conklin et al., Nature 363, 274-276 (1993) described, for the first time, a hybrid in which the 5 C-terminal amino acids of Gαq had been replaced by the corresponding Gαi sequence (Gαqi5), thus making possible a recoupling of normally Gαi-coupled receptors to the Gαq signal transduction pathway. WO 99/14344 and Brown et al., Yeast 16, 11-22 (2000) demonstrate that this same approach also works in yeast. In this case, the five C-terminal amino acids of Gpa1p were replaced by the corresponding amino acids of all human Gα proteins. The use of these hybrids called "transplants" makes it possible to couple numerous mammalian GPCRs to the mating pathway of yeast.

The yeast strains used here carry deletions in the SST2, FAR1 and, depending on the mating type of the cell, STE2 or STE3 genes. SST2, a member of the family of RGS proteins, is deleted in order to prevent down-regulation of the signal. Deletion of FAR1 enables cell growth to continue even under conditions under which the pheromone response pathway is switched off. STE2 or STE3 is switched off in order to prevent unwanted competition for the heterotrimeric G protein. The GPA1 gene was replaced in the yeast genome by the above-described transplants. Expression of said transplants under the control of the GPA1 promoter at the natural gene locus ensures that the stoichiometry of the heterotrimeric G protein is retained.

The action of at least one GPCR-dependent signal transduction pathway of a biological organism may be modified in an inhibitory or stimulatory way. A chemical compound has an inhibitory action when the signal transduction pathway-dependent measurable signal is weaker in the presence than in the absence of a chemical compound. Compounds which cause such an action are also referred to as antagonists. On the other hand, a chemical compound has a stimulator action when the signal transduction pathway-dependent measurable signal is stronger than in the absence of said chemical compound. Such compounds are also referred to as agonists. The use of the promoters of the genes FUS1, FUS2 (Cismowski et al., Nat Biotechnol 17, 878-883 (1999); Frederickson, Nat Biotechnol 17, 852-853 (1999)) and YNL279w (WO 02/40660) for functional assays in *Saccharomyces cerevisiae* has been described.

There is increased expression of said genes as response to a stimulation of the pheromone response pathway by mating factor. If a promoter element of one of these genes is then functionally linked to a structural gene, expression of said structural gene (also referred to as reporter gene) can be regulated via the yeast signal transduction pathway described. Such reporter genes are usually endogenous growth markers such as HIS3 or other auxotrophic marker genes (e.g. URA3, LEU2, ADE2, LYS1 or TRP1), which permit cell growth in a correspondingly depleted medium in the event of stimulated signal transduction pathway or genes which impart resistance or sensitivity to particular substances (e.g. CYH2 or G418R). However, is it also possible to use reporter genes which code for intercellular enzymes, such as β-galactosidase (LacZ), or "green fluorescent protein" (GFP), or for secreted enzymes such as phosphatases (PHO5). If the reporter used is CAN1, the cells grow in canavanin-containing medium. In the presence of activators (agonists) of a heterologously expressed GPCRs, the CAN1 gene is expressed so that the cells can no longer grow in canavanin-containing medium. Addition of an inhibitor (antagonist) leads to growth of the cultures in this selection medium.

The yeast GPCR assays described in the literature usually utilize only one reporter gene, mainly HIS3 or LacZ (Price et al., Mol Cell Biol 15, 6188-6195 (1995); Price et al., Molecular Pharmacology 50, 829-837 (1996); Campbell et al., Bioorg.Med.Chem.Lett. 9, 2413-2418 (1999); Pausch, Trends Biotechnol 15, 487-494 (1997)) under the control of the FUS1 promoter (FUS1-HIS3 or FUS1-lacZ). If FUS1-HIS3 is used, activation of the signal transduction pathway is measured as turbidity of the yeast culture in a liquid medium without histidine. Experiments of the inventors demonstrated that the single growth readout gave a signal-to-background ratio of approx. 30-50:1 in liquid culture (see FIGS. 1*a* and 3). β-Galactosidase liquid assays using chlorophenol red β-D-galactopyranoside (CPRG) as enzyme substrate exhibited, after stimulation, a signal increased by approx. 2-3 times above background (see also FIG. 1*b*). In an effort to further increase the measurement window, both reporter genes were used in a yeast cell simultaneously, since this should multiply the two measured signals. FIG. 1*c* illustrates this principle. This double reporter gene assay consequently improved the signal-to-background ratio to approx. 100-150:1. Brown et al., Yeast 16, 11-22 (2000) describe a similar assay. Here too, FUS1-HIS3 and FUS1-lacZ are utilized simultaneously in a β-galactosidase liquid assay using CPRG as substrate. CPRG is added here during the entire period of stimulation of the receptor with ligand. In contrast, CPRG is added in this method together with a detergent in buffered solution only after stimulation of the receptor with ligand, resulting in a marked improvement of the β-galactosidase measurement. For if, on the one hand, CPRG is present during ligand-induced growth, the latter is readily inhibited, and, on the other hand, CPRG can reach the cell interior through the plasma membrane only with difficulty. Both problems are avoided if CPRG is added together with a detergent capable of disrupting the plasma membrane, only after growth has finished.

In a preferred embodiment, the method utilizes a double reporter gene assay, one reporter being a growth marker and the other reporter gene being an enzyme or GFP. Only this combination of growth, a logarithmic event, and the more or less linearly induced expression of a measurable enzyme or fluorescent protein leads to the described amplification of the signal, i.e. a large measurement window.

EP 0 708 922 B1 (Acadia Pharmaceuticals) also describes a method based on growth as response to receptor stimulation. In this case, the ligand-stimulated receptor-expressing cells only grow faster than the nonstimulated cells (cf. FIG. 2 and FIG. 10 in EP 0 708 922 B1). In the invention described herein, however, such nonstimulated yeast cells do not grow at all (see examples listed (e.g. FIG. 3B, left graph)). EP 0 708 922 B1 also uses the activity of the heterologously expressed enzyme β-galactosidase as measurable signal. Here, however, LacZ is expressed constitutively, i.e. the enzyme activity measured is only a measure for the number of cells grown as response to stimulation of the signal transduction pathway by ligand, but not a measure for the strength of signal transduction pathway stimulation. In contrast, LacZ expression in the invention described herein is under the control of a promoter induced by the pheromone response pathway (e.g. FUS1 or YNL279w). FIG. 3A illustrates that, even with the same number of yeast cells (left-hand graph), the measurable activity of β-galactosidase depends on the amount of ligand added, i.e. on the strength of signal transduction pathway stimulation (right-hand graph).

According to EP 0 708 922 B1 (cf. p. 10), "amplification" of cells means "the growth of receptor-transfected cells, in particular in comparison with the growth of cells not transfected with the receptor", i.e. both receptor-transfected and nontransfected cells can grow, except that transfected cells grow faster after stimulation with ligand. The figures on p. 33 and p. 44 illustrate this. In the cell lines described, there is no reporter construct whose expression makes growth possible at all. The only modification making growth possible is the ligand-stimulated overexpressed receptor.

According to the preferred embodiment, however, a double selection is conducted: the nutrient medium lacks uracil and histidine, substances which the yeast strains used here need for living. Since we use the URA3 gene as selective marker on our receptor plasmids, cells lacking the receptor plasmid cannot grow at all.

The receptor DNA-transfected cells, too, can in principle not grow on said nutrient medium unless they are stimulated by the presence of ligand. Only when the ligand binds is the reporter gene HIS3 expressed and the cells are capable of growing on said nutrient medium.

In principle, a yeast strain which has been transfected with a receptor, but which does not carry any growth markers such as HIS3 as reporter gene, does not respond with growth.

The method described may be used both in single-receptor format and in multiple-receptor format (multiplex format). The advantages of this assay become particularly noticeable in the multiple-receptor format. FIG. 1c is intended to illustrate this. Theoretically, a single yeast cell expressing a particular receptor should be sufficient, if contacted by the appropriate ligand (a chemical compound or the natural ligand), to "rise" from the background of the other, nonresponding yeast cells as response to the stimulation. This brings advantages for high throughput screening, since this method allows a plurality of GPCRs to be screened simultaneously. Especially for orphan GPCRs whose importance for the pharmaceutical industry is not clear from the outset, the method described herein minimizes the investment of time and money by the company. Since the Gα subunits to which GPCRs couple are also unknown, the present method also provides the possibility of testing one or more orphan GPCRs in a plurality of transplant strains simultaneously.

DESCRIPTION OF THE FIGURES

FIG. 1 illustrates the principle of the double reporter gene assay in multiple-receptor format.

FIG. 7 explains carrying out an assay in multiple-receptor format.

MATERIAL AND METHODS

Figure 1A:
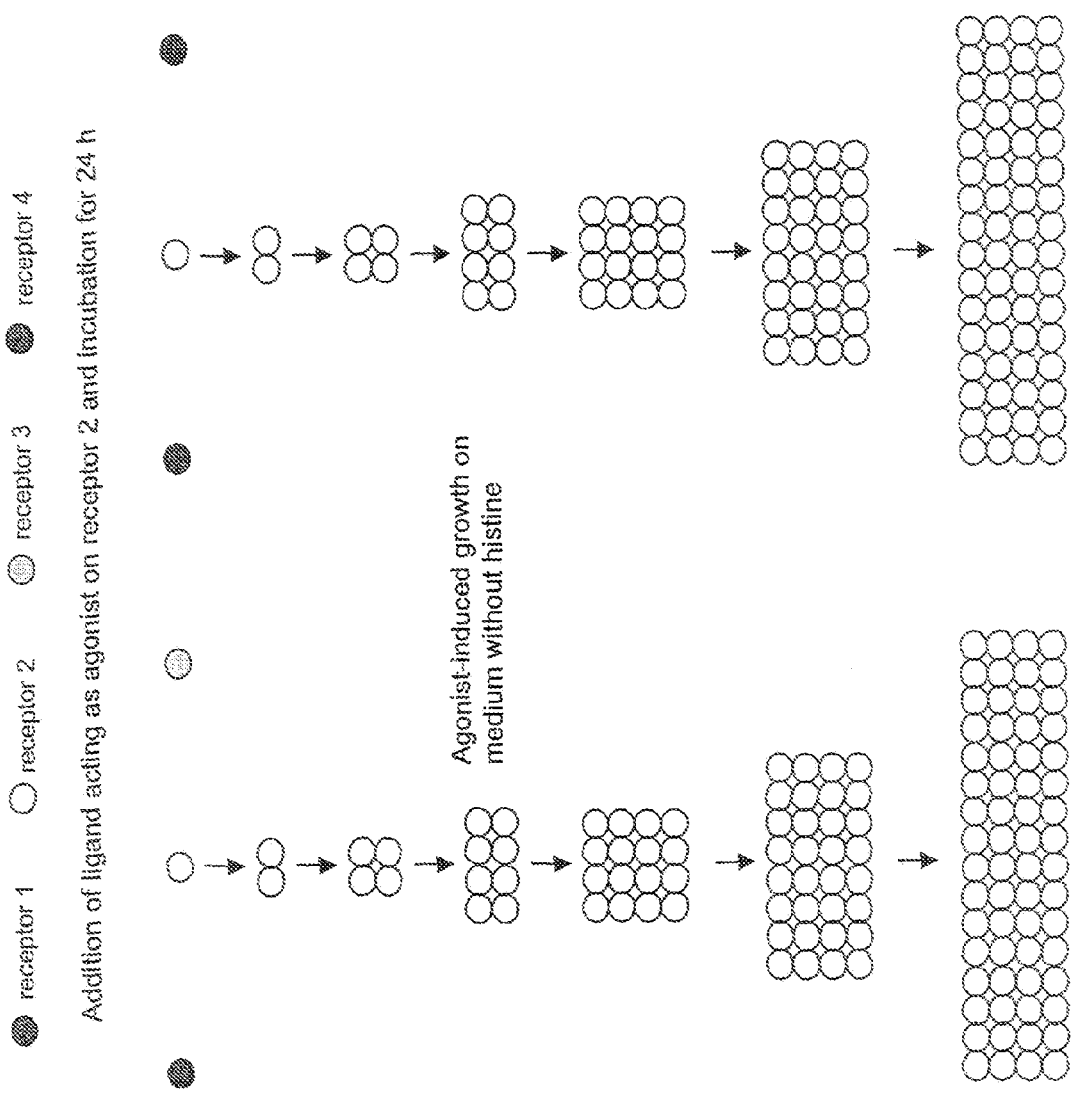
FIG. 1a depicts an agonist-induced growth readout.
Figure 1B:
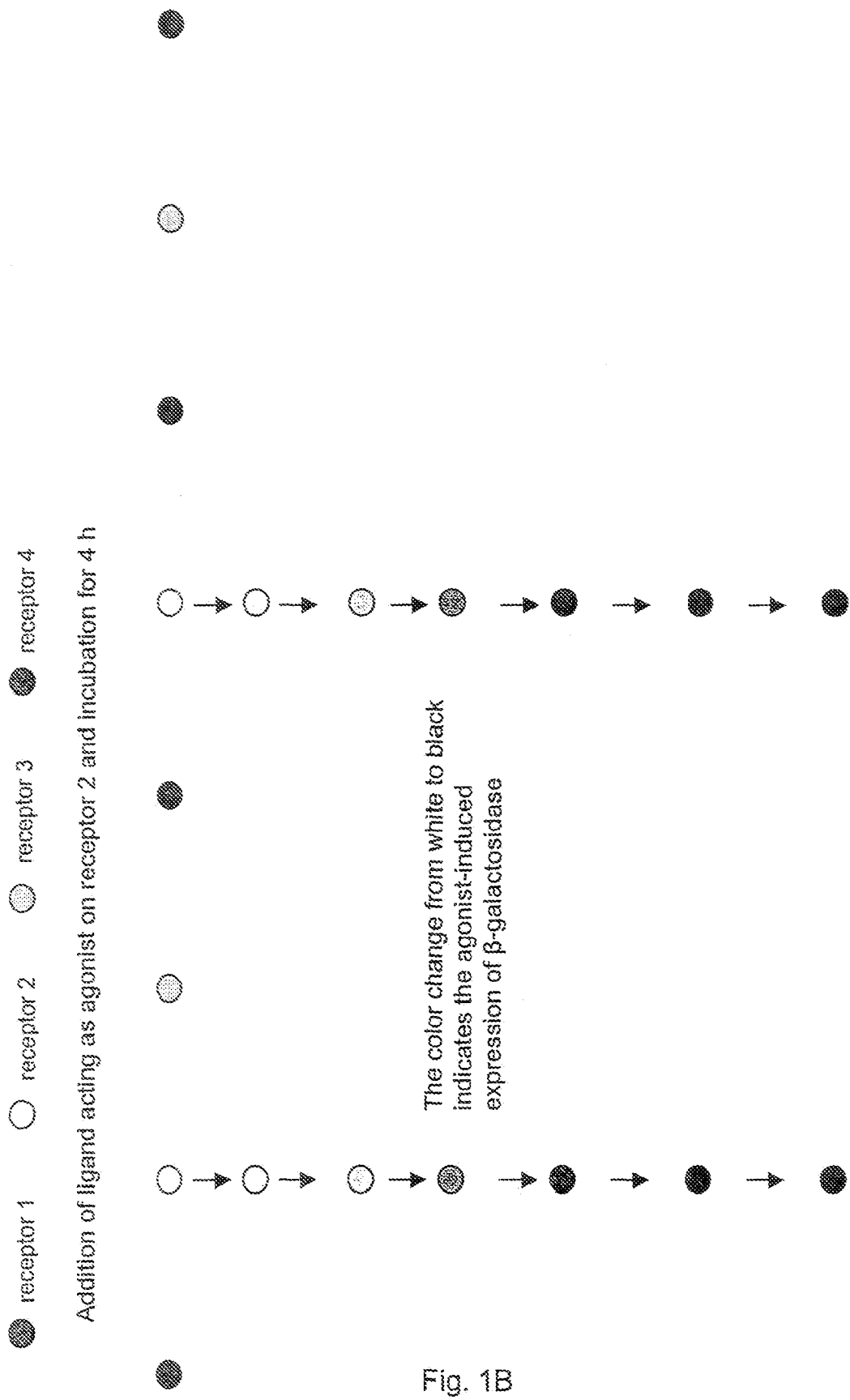
FIG. 1b is an angonist-induced β-galactosidase-mediated color readout. Finally.
Figure 1C:
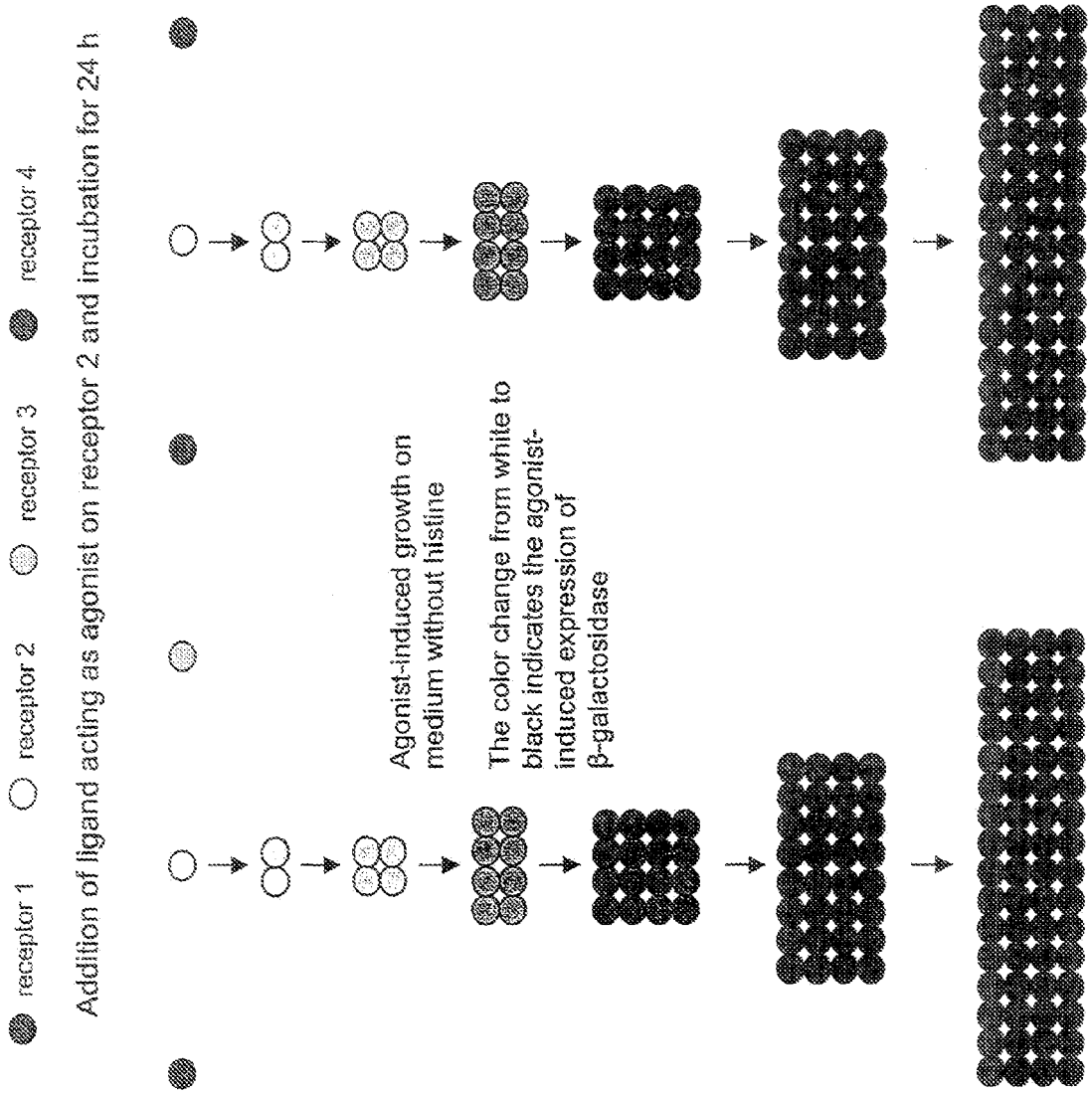
FIG. 1c depicts the double agonist-induced growth and color readout.
Figure 2A:
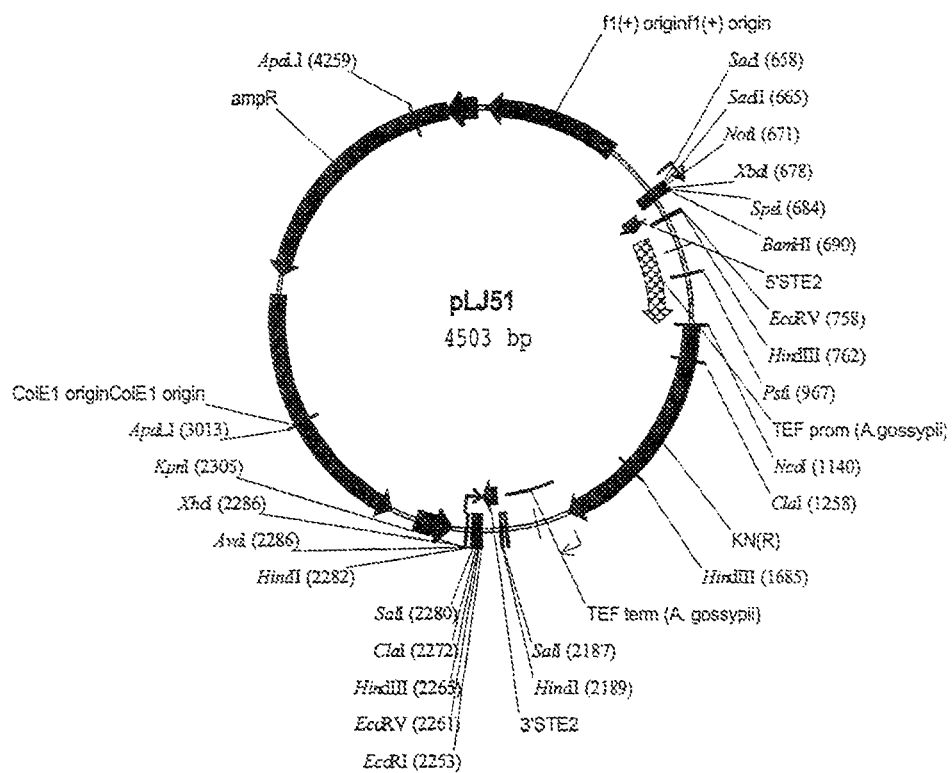
FIGS. 2A-D depict plasmids which were used for constructing the strains based on the YNL279w promoter.
Figure 2B:
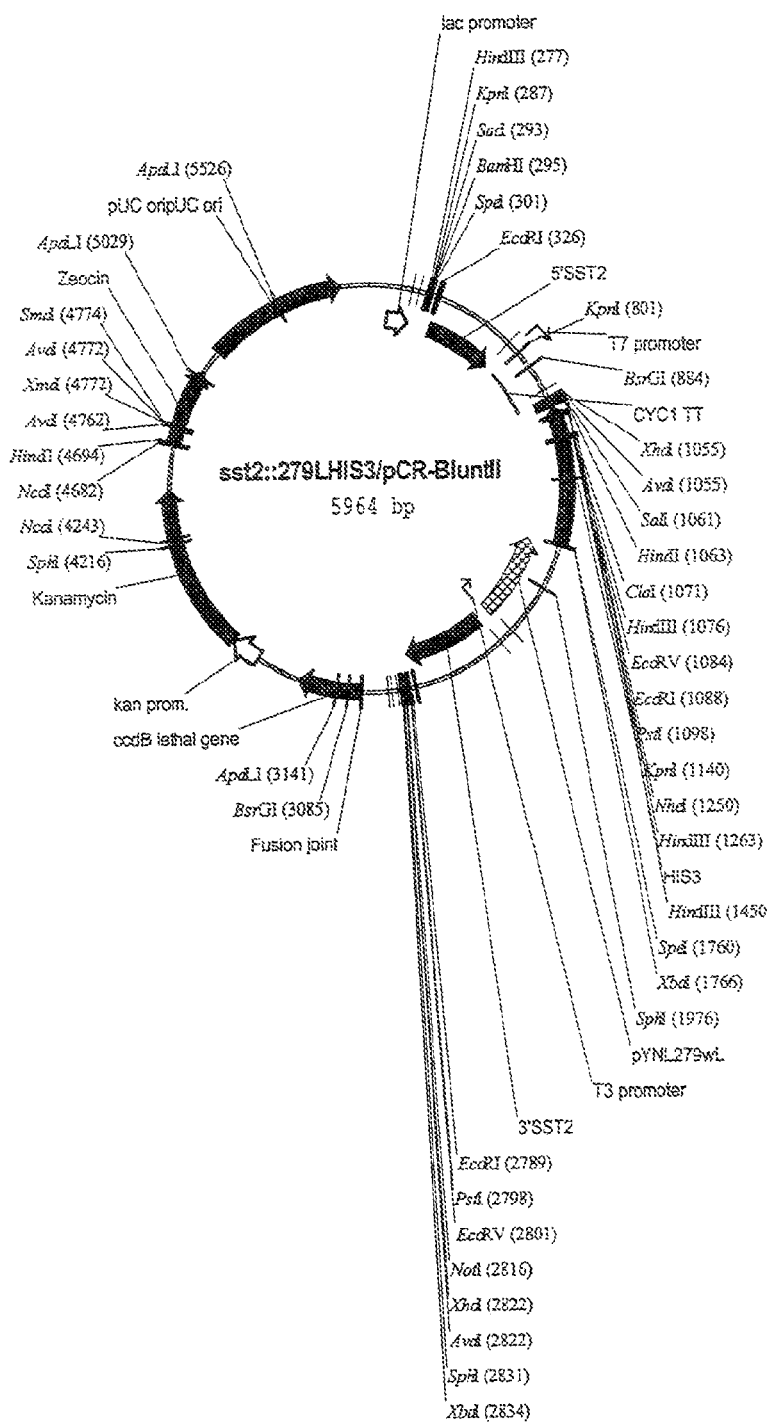
Figure 2C:
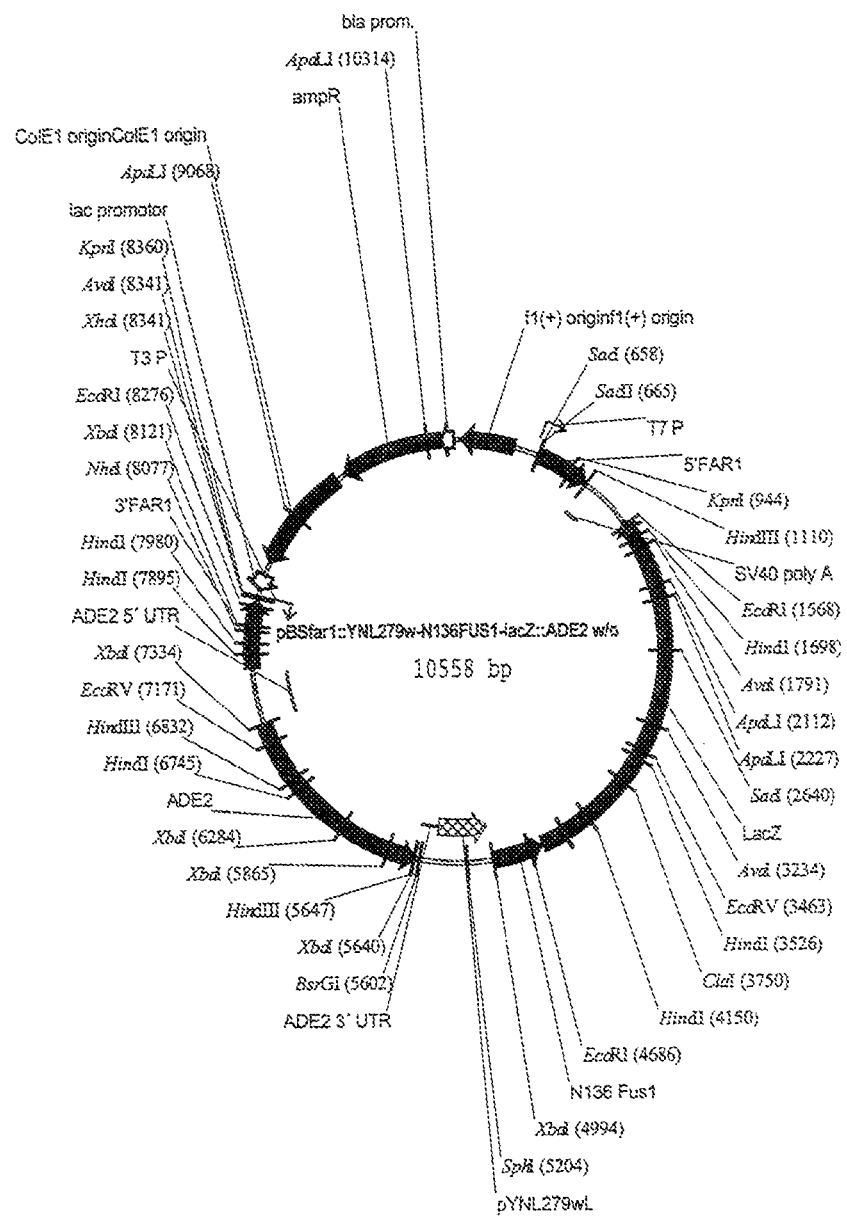
Figure 2D:
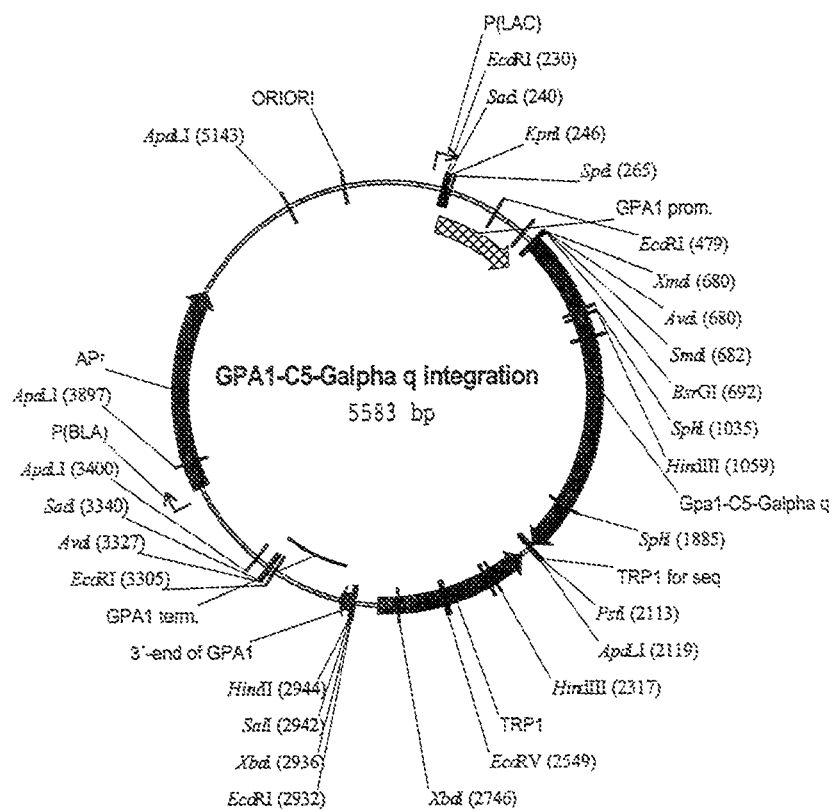

Plasmids and Yeast Genetics:

All molecular-biological and genetic manipulations were carried out according to standard methods (Ausubel et al., Current Protocols in Molecular Biology, Wiley & Sons, New York; Guthrie und Fink, Guide to Yeast Genetics and Molecular Biology, Methods in Enzymology, Academic Press, San Diego).

Expression Constructs for Receptors:

All expression constructs are based on the episomal 2μ yeast E. coli shuttle vector p426GPD (Mumberg et al., Gene 156, 119-122 (1995)). cDNA sequences which code for the human G protein-coupled receptors are cloned in this vector between the GPD promoter and the CYC terminator in order to achieve high, constitutive expression in yeast cells. The following human GPCRs were cloned into this vector: EDG1 receptor (GenBank NM_001400), EDG5 receptor (GenBank NM_004230), bradykinin B2 receptor (GenBank NM_000623), M1 muscarinic receptor (GenBank NM_000738), somatostatin SSTR2 receptor (GenBank NM_001050). M3 muscarinic receptor (GenBank NM_000740).

Yeast Strains:

All yeast strains are based on *Saccharomyces cerevisiae* wild-type strain W303-1a, described under ATCC number 208352.

Genotype: MATa, ade2-1, ura3-1, his3-11, trp1-1, leu2-3, leu2-112, can1-100

Two different sets of yeast strains were used. One set derives from YLJ21 and utilizes the promoter of the FUS1 gene for expressing the reporter gene, while the other set derives from YSG13 and utilizing the promoter of the YNL279w gene.

The yeast strain YLJ21 was provided by Ekkehard Leberer.

Genotype: MATa, ste2::KanR sst2::ura3$^{FOA}$ far1::hisG FUS1::HIS3 mfa2::FUS1-lacZ::ura3$^{FOA}$ade2-1, ura3-1, his3-11, trp1-1, leu2-3, leu2-112, can1-100

Activation of the pheromone response pathway can be measured with the aid of the two reporter genes FUS1::HIS3 and FUS1-lacZ which have been integrated at the HIS3 gene locus and MFA2 gene locus respectively. The FAR1 gene has been replaced by a hisG repeat so that the cells can continue to grow, even when the pheromone response pathway has been activated. The SST2 gene was replaced by the URA3 gene in order to prevent down-regulation of the G protein signal due to the GTPase function of Sst2p. The ura3 marker was in each case recovered again by selecting on 5-fluoro-orotic acid-containing medium. The gene STE2 which codes for the a-factor receptor has been replaced by a KanR gene.

The yeast strain YSG13 was prepared as follows:
Genotype:
MATa, ste2::KanR sst2::pYNL279w-HIS3 far1::pYNL279w-N136FUS1-lacZ::ADE2 ade2-1, ura3-1, his3-11, trp1-1, leu2-3, leu2-112, can1-100

Strain Construction:
ste2::KanR

In order to replace the yeast STE2 gene by a kanamycin resistance gene, plasmid pLJ51 was cut with BamHI and EcoRI and transformed into the wild-type yeast strain W303-1a. Selection was carried out on YPD+G418 medium.

sst2::pYNL279w-HIS3

In another step, the yeast SST2 gene was replaced by a cassette which allows expression of the HIS3 gene under the control of the YNL279w promoter. For this purpose, plasmid sst2::279LHIS3/pCR-Bluntil was cut with BamHI and NotI and transformed. Selection was carried out on SC/Gluc-His+α factor medium.

far1::pYNL279w-N136FUS1-lacZ::ADE2

The FAR1 gene was then replaced by a cassette which allows expression of the 136 N-terminal amino acids of Fus1p fused to β-galactosidase under the control of the YNL279w promoter. For this purpose, plasmid pBSfar1::YNL279w-N136FUS1-lacZ::ADE2 w/o was cut with SacII and XhoI and transformed. Selection was carried out on SC/Gluc-Ade medium.

Correct integration of all fragments into the genome was always checked by means of PCR.

Introducing the transplants into YLJ21 and YSG13:

Starting from the strains YLJ21 and YSG13, the last 5 amino acids of the yeast G protein α-subunit Gpa1 in the yeast genome were finally replaced by the last 5 amino acids of the human G protein α-subunits. For this purpose, for example for constructing the yeast strain YEW3, the plasmid GPA1-C5-Galpha q integration was cut with SacI and transformed into yeast strain YLJ21. Selection was carried out on SC/Gluc-Trp medium. The other transplants were integrated in the same way. Table 1 lists the various transplants and yeast strains derived therefrom.

TABLE 1

G protein transplants

| GPA1/GαX transplant | Represents human G protein α-subunit | 5 C-terminal amino acids | FUS1 promoter | YNL279w promoter |
|---|---|---|---|---|
| GPA1 | — | KIGII (SEQ ID NO: 1) | YLJ21 | YSG13 |
| i1 | t, i1, i2 | DCGLF (SEQ ID NO: 2) | YEW11 | YEW25 |
| i3 | i3 | ECGLY (SEQ ID NO: 3) | YEW7 | YEW21 |
| o | o1, o2 | GCGLY (SEQ ID NO: 4) | YEW8 | YEW22 |
| z | z | YIGLC (SEQ ID NO: 5) | YEW12 | YEW26 |
| q | q, 11 | EYNLV (SEQ ID NO: 6) | YEW3 | YEW17 |
| 14 | 14 | ENFLV (SEQ ID NO: 7) | YEW6 | YEW20 |
| 16 | 15, 16 | EINLL (SEQ ID NO: 8) | YEW2 | YEW16 |
| 12 | 12 | DIMLQ (SEQ ID NO: 9) | YEW13 | YEW27 |
| 13 | 13 | QLMLQ (SEQ ID NO: 10) | YEWI4 | YEW28 |
| s | s1, s2 | QYELL (SEQ ID NO: 11) | YEW1 | YEW15 |

Double Reporter Gene Assay:

The human GPCRs cloned into vector p426GPD are transformed into the appropriate yeast strain and incubated on SC selection plates without uracil and with 2% glucose as carbon source (SC/Gluc-Ura) at 30° C. for 3 days. The single cell colonies thus obtained are then utilized in order to inoculate 2 ml overnight cultures in SC/Gluc-Ura. The next day, the cells are diluted 1:100 in SC/Gluc-Ura-His pH 6.8. In the case of yeast strains using the FUS1 promoter for reporter gene expression, 2-10 mM 3-aminotriazole (3-AT, Sigma) are additionally added to said medium. In each case 90 μl of the diluted cell suspension are pipetted into a well of a 96-well microtiter plate, which already contains 10 μl of the ligand to be studied. The plates are incubated with or without shaking at 30° C. for 5-24 h. This is followed by adding to each well 50 μl of assay mix. The assay mix consists of 150 μg/ml digitonin (Sigma), 300 μg/ml chlorophenol red β-D-galactopyranoside (CPRG, Roche), 300 mM sodium phosphate buffer pH 6.7. After incubation with or without shaking at 30° C. for 2 h, β-galactosidase activity is measured as absorption at 574 nm in a spectrophotometer (Spectramax Plus, Molecular Devices). The data are analyzed and dose-response curves are drawn using the Graphpad Prism 3.0 computer program. All measurements are averages from triplicate determinations.

Example 2

Figure 3:
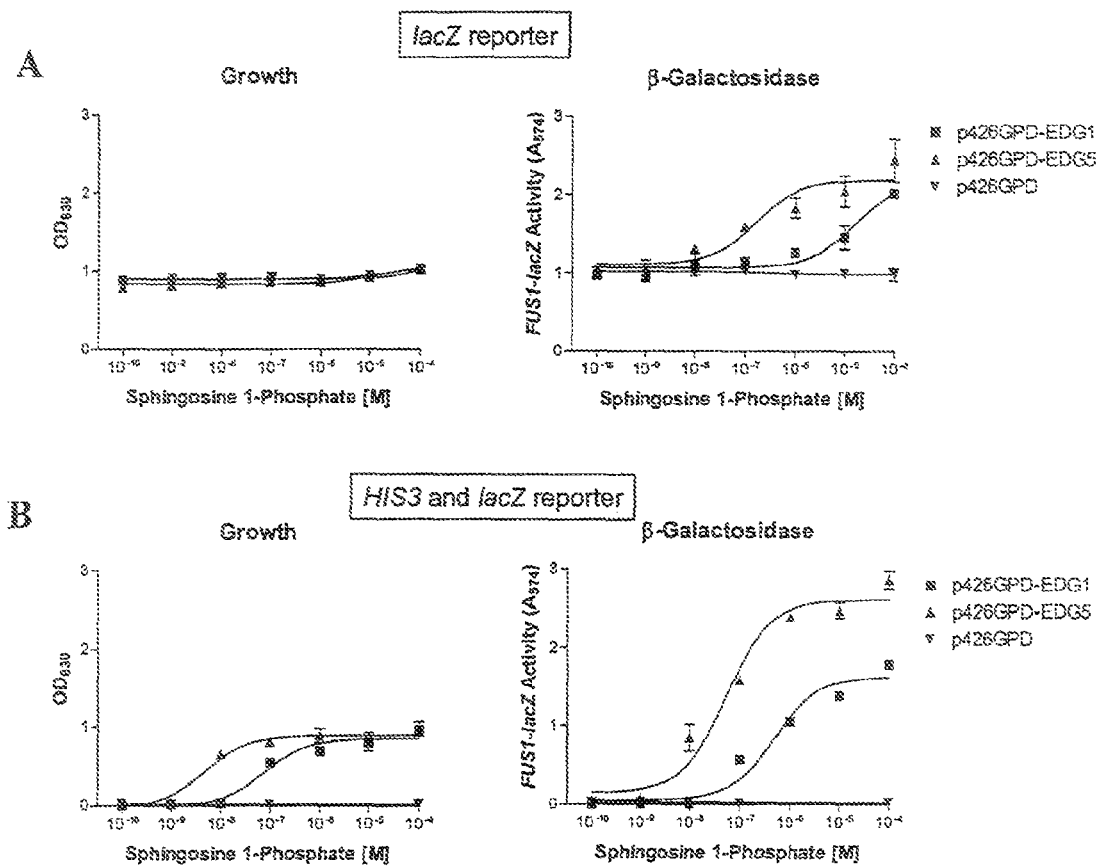
FIG. 3 illustrates how the double reporter gene assay improves the performance of the yeast liquid assay, compared to utilizing only one reporter gene.

Comparison Between the Use of One Reporter Gene Alone or Two Reporter Genes Simultaneously Yeast strain YLJ21 was transformed either with the empty vector p426GPD or with human GPCRs EDG1 and EDG5 which had been cloned into p426GPD. The transformed yeasts were then cultivated in 2 ml of SC/Gluc-Ura at 30° C. overnight. The next day, the cultures were diluted 1:100 in SC/Gluc-Ura-His pH 6.8 medium without (FIG. 3A) or with 2 mM 3-AT (FIG. 3B). In each case 90 µl of the diluted cell suspension are pipetted into a well of a 96-well microtiter plate, which already contains in each case 10 µl of a serial dilution of sphingosine 1-phosphate (Biomol) or pure water as control. The plates were incubated with shaking (700 rpm) at 30° C. for 23 h. The turbidity resulting from growth of the yeast cells was measured at 630 nm in the photometer (FIGS. 3A and B, in each case left-hand graph). This was followed by adding 50 µl of assay mix per well. After incubation with shaking at 30° C. for 2 h, β-galactosidase activity was measured as absorption at 574 nm in the photometer.

The left-hand graph of FIG. 3A indicates that, when using FUS1-HIS as reporter construct, no dose-response curve is visible without addition of 3-AT. The FUS1 promoter leads to quite a high background signal on medium without histidine, even without stimulation of the signal transduction pathway, i.e. the promoter is not strictly regulated. If, in contrast, 2 mM 3-AT, a competitive inhibitor of His3p, is added, the background signal is suppressed and the level of the measured signal is dependent on the amount of sphingosine 1-phosphate (Ancellin et al., J Biol Chem 274, 18997-19002 (1999)) in the medium when EDG1 or EDG5 are expressed (FIG. 3B, left-hand graph). FIG. 3A, right-hand graph, illustrates the fact that LacZ reporter gene also leads to an acceptable dose-response curve, but the measurement window is very small. As FIG. 3B, right-hand graph, indicates, simultaneous use of HIS3 and LacZ results in a signal-to-background ratio which is several times better. Overall, this experiment indicates that the human GPCRs EDG1 and EDG5 can couple via the yeast-endogenous Gα subunit Gpa1p to the pheromone response pathway.

Example 3

Figure 4:
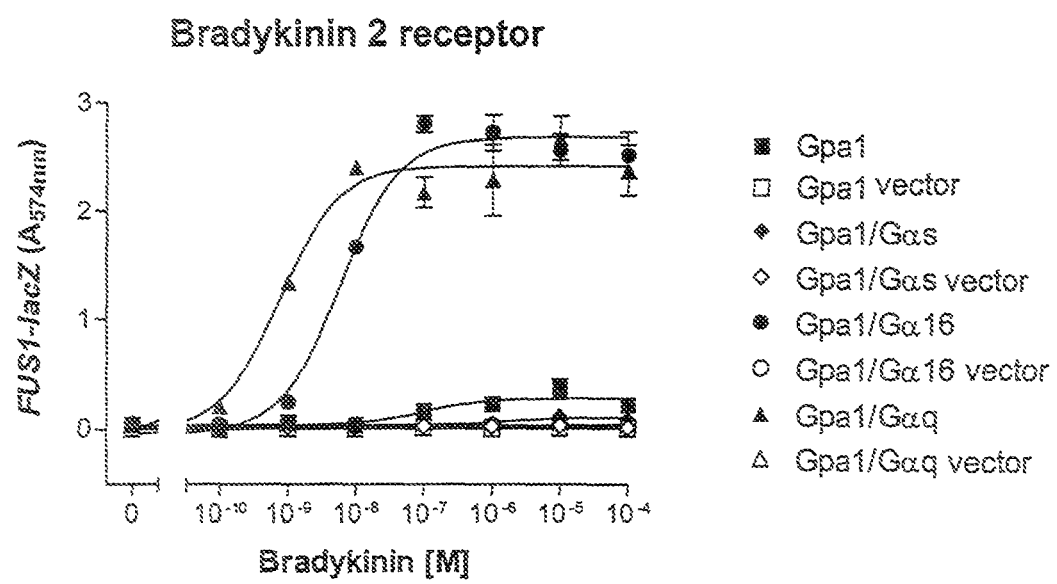
FIG. 4 indicates binding of the human bradykinin B2 receptor to the yeast signal transduction pathway as a function of the Gα transplant used. The empty vector p426GPD was always used as control.

Double Reporter Gene Assay with Binding of the Human Bradykinin B2 Receptor to the Signal Transduction Pathway of Yeast via Gα Transplants Yeast strains YLJ21 (Gpa1), YEW1 (Gpa1/Gαs), YEW2 (Gpa1/Gα16) and YEW3 (Gpa1/Gαq) were transformed either with the empty vector p426GPD or with the human bradykinin B2 receptor cloned into p426GPD. The assay was carried out in the presence of 2 mM 3-AT under standard conditions, as described above. The ligand used was the natural agonist bradykinin (Sigma); incubation was carried out for 20 h. FIG. 4 illustrates the fact that the bradykinin B2 receptor can hardly bind to the pheromone response pathway at all if only Gpa1p is available. If, in contrast, the yeast expresses the Gα transplants Gpa1/Gα16 or Gpa1/Gαq, binding of the receptor to said signal transduction pathway has been successful. Gpa1/Gαq allows the most effective coupling, which was to be expected, since the human bradykinin B2 receptor couples to Gαq in its natural cellular environment (Hall, Pharmacol.Ther. 56, 131-190 (1992)).

Example 4

Use of the Double Reporter Gene Assay for Antagonist Assays

Figure 5:
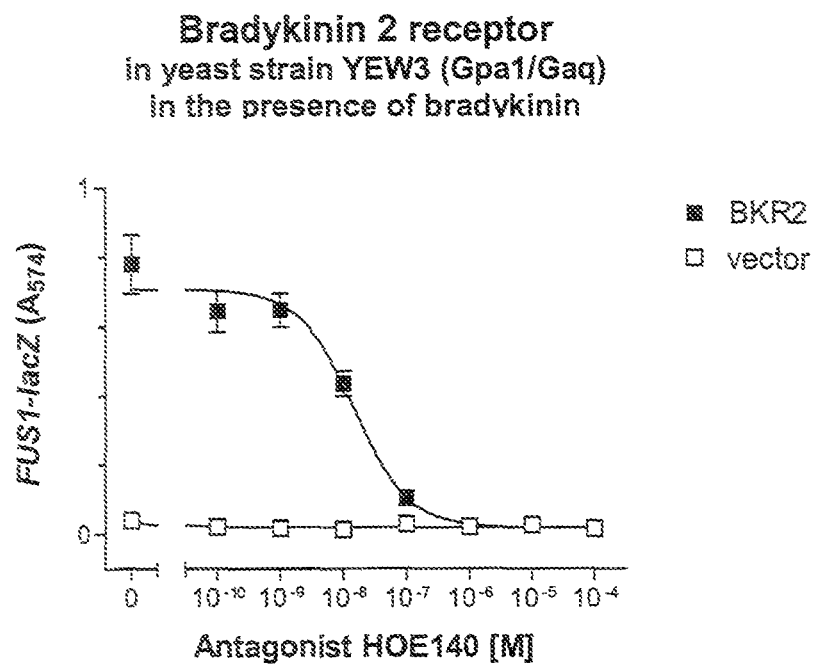
FIG. 5 indicates that the double reporter gene assay may also be used for screening antagonists. Examples shown here are the human bradykinin B2 receptor and the empty vector control.

The yeast strain YEW3 (Gpa1/Gαq) was transformed either with the empty vector p426GPD or the human bradykinin B2 receptor cloned into p426GPD. The assay was carried out in a similar way to example 2. The only difference was that each well of the test plate contained 1 nM bradykinin agonist, to which dilutions of the antagonist HOE140 (Sigma; Hall, Gen.Pharmacol. 28,1-6 (1997)) had been added. FIG. 5 indicates that increasing amounts of HOE140 suppress the signal caused by bradykinin to the background level. Thus the double reporter gene assay is also suitable for antagonist assays.

Example 5

Comparison Between the Promoters of FUS1 and YNL279w

The yeast strains YEW3 (Gpa1/Gαq, FUS promoter) and YEW17 (Gpa1/Gαq, YNL279w promoter) were transformed either with the empty vector p426GPD or with the human bradykinin B2 receptor cloned in p426GPD. The assay was carried out, in the case of YEW3, in the presence of 2 mM 3-AT and, in the case of YEW17, without 3-AT, under standard conditions as described above. After addition of assay mix, β-galactosidase activity was measured after 2 h and again after 29 h.

Figure 6A:
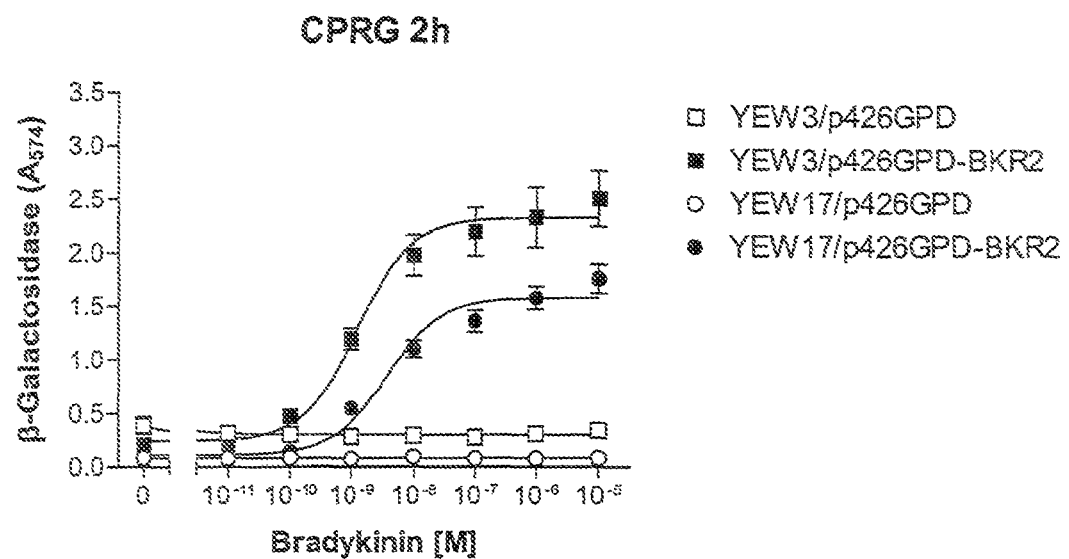
FIGS. 6A and B indicate that using the YNL279w promoter produces, even after 29 h of incubation with the enzyme substrate, distinctly less background signal than using the FUS1 promoter.
Figure 6B:
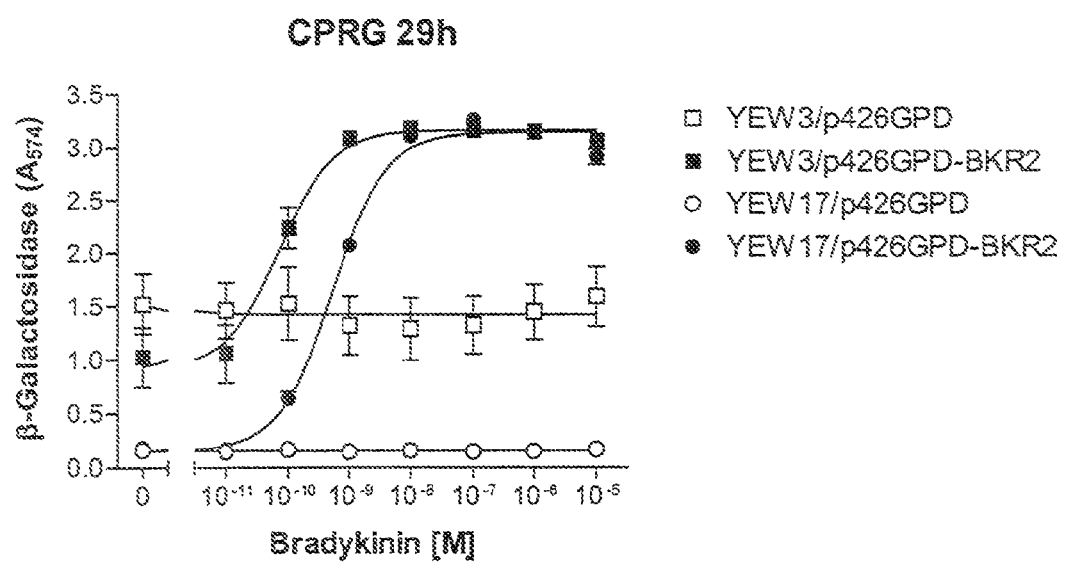

As FIG. 6A and, more impressively, FIG. 6B indicate, the background signal of the receptor-transformed strain or else of the strain transformed with the empty control vector increases considerably with time in the case of the FUS1 promoter, even though 3-AT was present in the medium. In the case of the YNL279w promoter, the background signal does not substantially change with time. The addition of 3-AT is not necessary. From this, it can be concluded that YNL279w is very strictly regulated. This proves particularly advantageous in high throughput assays, since the measurement need not be timed precisely, thereby making possible more flexible working.

Example 6

Carrying Out an Assay in Multiple-receptor Format (Multiplex Format)

Figure 7A:
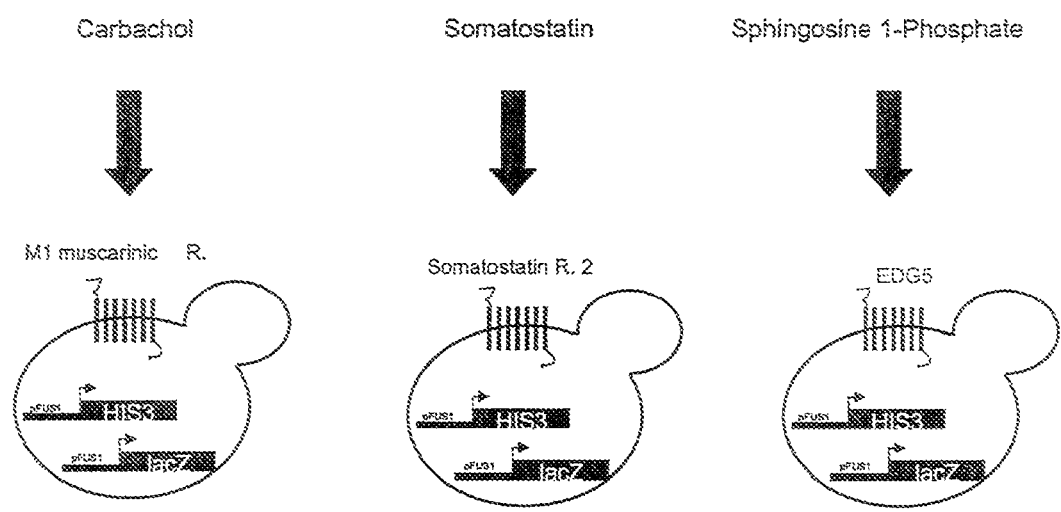
FIG. 7A illustrates the fact that the various GPCRs are expressed in each case in a separate yeast strain, not all of them together in one.
Figure 7B:
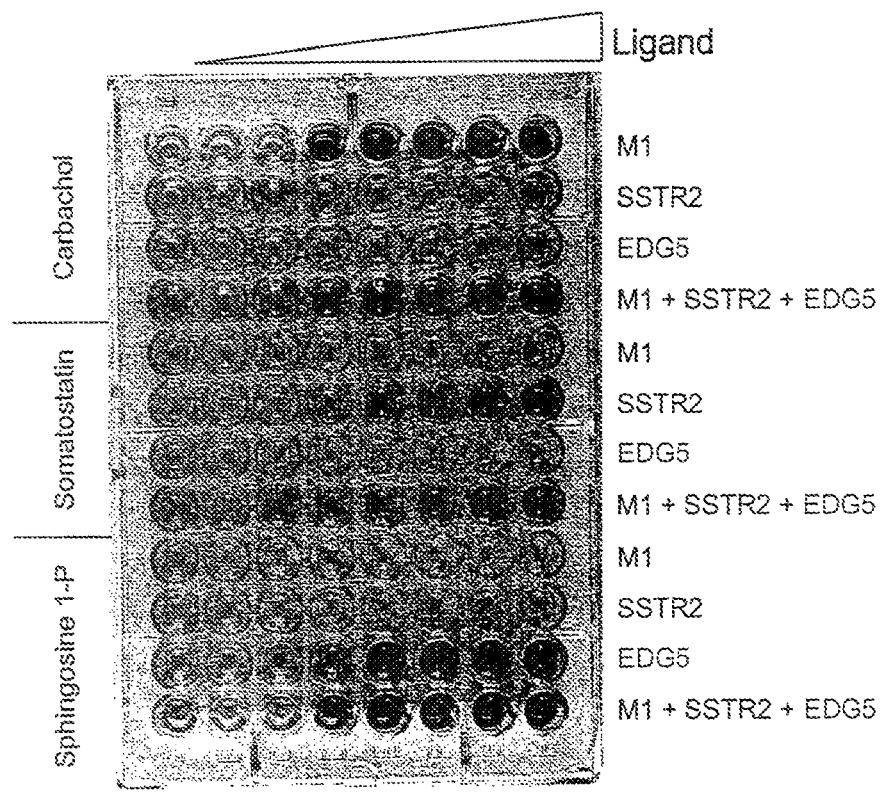
FIG. 7B demonstrates the performance of an assay in multiple-receptor format in comparison with single-receptor format in a microtiter plate.

YEW3 (Gpa1/Gαq) was transformed with the human M1 muscarinic receptor and YLJ21 (Gpa1) was transformed with somatostatin receptor 2 and EDG5. The receptors had been cloned into p426GPD. The procedure was carried out according to the standard method described above. The receptors were tested either individually or in a mixture. In the case of the mixture, the same overnight cultures as for the individual tests were used. They were mixed only at the 1:100 dilution in SC/Gluc-Ura-His pH 6.8, i.e. the mixture thus contains overall three times as many cells as the individual tests. FIG. 7A is intended to illustrate that all of the receptors have been expressed individually, i.e. not together in one cell. Incubation with the ligands carbachol (Sigma; dilution $10^{-8}$M to $10^{-2}$M), somatostatin-14 (Bachem; $10^{-10}$M to $10^{-4}$M) and sphingosine 1-phosphate (Biomol, $10^{-10}$M to $10^{-4}$M) was carried out for 24 h. As FIG. 7B illustrates, the agonists can also be detected in the mixture.

Example 7

Comparison of Two Detection Methods for β-galactosidase

Figure 8:
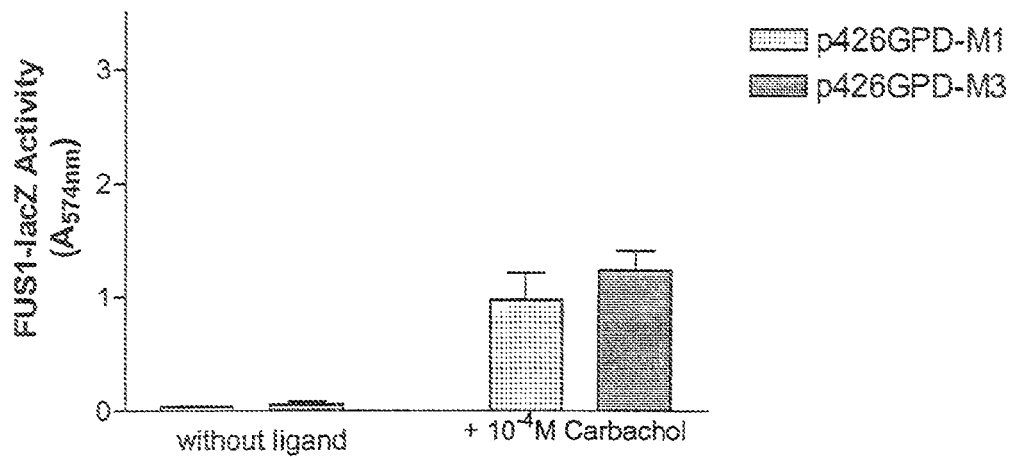
FIG. 8 indicates that the performance of the assay increases when the enzyme substrate CPRG is added together with detergent only after incubating with ligands.
Figure 8:
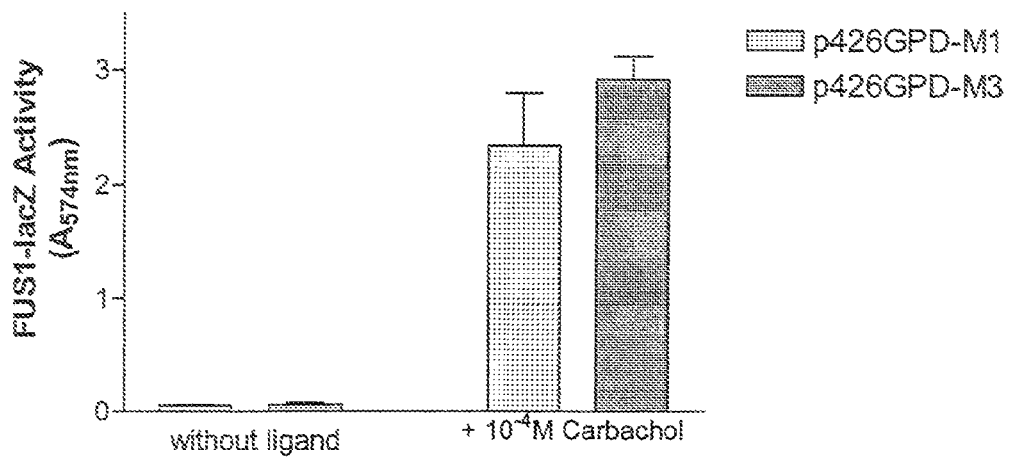

Conventionally, a yeast CPRG assay is carried out in such a way that CPRG is present in the medium for the entire period in which the receptor-transformed yeast cell is in contact with ligand (Brown et al., Yeast 16, 11-22 (2000) and WO 99/14344). FIG. 8 depicts a comparison between this method and the method illustrated in the present invention.

YEW3 (Gpa1/Gαq) was transformed with the human M1 and M3 muscarinic receptors cloned in p426GPD. Overnight cultures were cultivated as described and then diluted 1:100 to $OD_{600}$ 0.02 in two different media. In one case (FIG. 8A), the cells were diluted in SC/Gluc-Ura-His, 2 mM 3-AT, 0.1 mg/ml of CPRG, 0.1 M sodium phosphate buffer pH 7. In the other case, the assay was carried out as described above in the presence of 2 mM 3-AT (FIG. 8B). The ligand used for the muscarinic receptors was carbachol. The assay was carried out for the data in FIG. 8A for 28 h, before analyzing the assay plate in the photometer. In the case of FIG. 8B, incubation was for 26 h, followed by addition of the assay mix. The measurement was carried out 2 h later.

As FIG. 8 illustrates, the addition of CPRG and a detergent, in this case digitonin, improves the performance of the assay considerably only after the incubation with ligand. Another advantage of the method described here is the fact that a possible interaction of CPRG during the long incubation with chemical compounds, especially during a screening, can be ruled out.

What is claimed is:

1. A method utilizing a double reporter gene assay for improving the signal-to-background ratio to identify an agent that modulates the activity of a target molecule comprising the steps of:
   a) contacting a yeast cell in a medium lacking histidine with a candidate compound, wherein the cell comprises the target molecule, and wherein the cell further comprises a growth marker reporter gene and an enzymatic reporter gene coding for an enzyme whose activity is detectable on the basis of conversion of a substrate, wherein the growth marker reporter gene is HIS3 gene under the control of FUS 1 promoter, and the enzymatic reporter gene is LacZ gene under the control of YNL279w promoter;
   b) adding the substrate chlorophenolred-β-D-galactopyranoside (CPRG) and a substance capable of permeabilizing the membrane of the cell after the contacting step a);
   c) measuring cell propagation and measuring the activity of the enzymatic report gene.

2. The method of claim 1, wherein the target molecule is a heterologous molecule.

3. The method of claim 2, wherein the heterologous molecule is selected from the group consisting of: an oligonucleotides, a polynucleotide, a nucleic acid, a polypeptide, a protein, and a protein fragment.

4. The method of claim 1, wherein the target molecule affects cellular propagation directly.

5. The method of claim 1, wherein the target molecule affects cellular propagation indirectly.

6. The method of claim 1, wherein the yeast cell is a *S. cerevisiae* cell.

7. A method of for identifying an agent that modulates the activity of at least one target molecule comprising the steps of:
   (a) contacting a first yeast cell in a medium lacking histidine with a first candidate compound, wherein the first cell comprises a first target molecule, and wherein the cell further comprises a growth marker reporter gene and an enzymatic reporter gene coding for an enzyme whose activity is detectable on the basis of conversion of a substrate, wherein the growth marker reporter gene is HIS3 gene under the control of FUS 1 promoter, and the enzymatic reporter gene is LacZ gene under the control of YNL279w promoter;
   (b) contacting a second yeast cell in a medium lacking histidine with a second candidate compound, wherein the second cell comprises a second target molecule, and wherein the cell further comprises a growth marker reporter gene and an enzymatic reporter gene coding for an enzyme whose activity is detectable on the basis of conversion of a substrate, wherein the growth marker reporter gene is the HIS3 gene under the control of the FUS 1 promoter, and the enzymatic reporter gene is the LacZ gene under the control of the YNL279w promoter, and wherein the first target molecule is different from the second target molecule;
   (c) adding the substrate chlorophenolred-β-D-galactopyranoside (CPRG) and a substance capable of permeabilizing the membrane of the cell after each of the contacting steps (a) and (b);
   (d) measuring cell propagation of the first cell and measuring the activity of the enzymatic reporter gene in the first cell; and
   (e) measuring cell propagation of the second cell and measuring the activity of the enzymatic reporter gene in the second cell.

8. The method of claim 7, wherein at least one of the first and second target molecules is a heterologous molecule.

9. The method of claim 8, wherein the heterologous molecule is selected from the group consisting of: an oligonucleotide, a polynucleotide, a nucleic acid, a polypeptide, a protein, and a protein fragment.

10. The method of claim 7, wherein at least one of the first and second target molecules affects cellular propagation directly.

11. The method of claim 7, wherein at least one of the first and second target molecules affects cellular propagation indirectly.

12. The method of claim 7, wherein at least one of the first and second yeast cells is a *S. cerevisiae* cell.

* * * * *

```
                          SEQUENCE LISTING

<160> NUMBER OF SEQ ID NOS: 11

<210> SEQ ID NO 1
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 1

Lys Ile Gly Ile Ile
1               5

<210> SEQ ID NO 2
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 2

Asp Cys Gly Leu Phe
1               5

<210> SEQ ID NO 3
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 3

Glu Cys Gly Leu Tyr
1               5

<210> SEQ ID NO 4
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 4

Gly Cys Gly Leu Tyr
1               5

<210> SEQ ID NO 5
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 5
```

Tyr Ile Gly Leu Cys
1               5

<210> SEQ ID NO 6
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 6

Glu Tyr Asn Leu Val
1               5

<210> SEQ ID NO 7
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 7

Glu Asn Phe Leu Val
1               5

<210> SEQ ID NO 8
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 8

Glu Ile Asn Leu Leu
1               5

<210> SEQ ID NO 9
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 9

Asp Ile Met Leu Gln
1               5

<210> SEQ ID NO 10
<211> LENGTH: 5
<212> TYPE: PRT
<213> ORGANISM: Artificial
<220> FEATURE:
<223> OTHER INFORMATION: 5 C-terminal amino acids of human G protein
      alpha-subunits

<400> SEQUENCE: 10

Gln Leu Met Leu Gln
1               5

<210> SEQ ID NO 11
<211> LENGTH: 5
<212> TYPE: PRT
<213> ORGANISM: Artificial
<220> FEATURE:

<223> OTHER INFORMATION: 5 C-terminal amino acids of human G protein
      alpha-subunits

<400> SEQUENCE: 11

Gln Tyr Glu Leu Leu
1               5